United States Patent [19]
Sampson et al.

[11] Patent Number: 6,054,274
[45] Date of Patent: Apr. 25, 2000

[54] METHOD OF AMPLIFYING THE SIGNAL OF TARGET NUCLEIC ACID SEQUENCE ANALYTE

[75] Inventors: Jeffrey R. Sampson, Burlingame; Douglas J. Dellinger, Sunnyvale, both of Calif.

[73] Assignee: Hewlett-Packard Company, Palo Alto, Calif.

[21] Appl. No.: 08/967,936

[22] Filed: Nov. 12, 1997

[51] Int. Cl.$^7$ .............................. C12Q 1/68; C12P 19/34
[52] U.S. Cl. .............................. 435/6; 435/7.1; 435/7.92; 435/91.1; 435/91.2; 536/23.1; 536/24.3; 536/24.33
[58] Field of Search .............................. 435/6, 7.1, 91.1, 435/91.2, 91.21, 7.4, 7.9, 7.92, 7.95; 536/23.1, 24.3, 24.33

[56] References Cited

U.S. PATENT DOCUMENTS

| | | | |
|---|---|---|---|
| 5,124,246 | 6/1992 | Urdea et al. | 435/6 |
| 5,354,668 | 10/1994 | Auerbach | 435/91.1 |
| 5,426,180 | 6/1995 | Kool | 536/25.3 |
| 5,591,609 | 1/1997 | Auerbach | 435/91.2 |
| 5,594,151 | 1/1997 | Stolowitz | 548/542 |
| 5,614,389 | 3/1997 | Auerbach | 435/91.2 |
| 5,648,245 | 7/1997 | Fire et al. | 435/91.1 |
| 5,714,320 | 2/1998 | Kool | 435/6 |
| 5,854,033 | 12/1998 | Lizardi | 435/91.2 |

FOREIGN PATENT DOCUMENTS

| | | |
|---|---|---|
| WO 96/33207 | 10/1996 | WIPO . |
| WO 97/19193 | 5/1997 | WIPO . |
| WO 97/42346 | 11/1997 | WIPO . |

OTHER PUBLICATIONS

Kessler, C., *Advances in Mutagenesis Research*, (Obe, G, editor), Berlin/Heidelberg: Springer–Verlag (1990), pp. 105–152.

Kornberg, A. and Baker, T.A. (editors), "DNA Polymerase 1 of *E. coli*", DNA Replication, W.H. Freeman Publishing (1992), p. 113–164.

Liu, Dongyu et al., "Rolling Circle DNA Synthesis: Small Circular Oligonucleotides as Efficient Templates for DNA Polymerases", *J. Am. Chem. Soc.*, vol. 118 (1996), pp. 1587–1594.

Antao, Vincent P. et al., "A Thermodynamic Study of Unusually Stable RNA and DNA Hairpins", *Nucleic Acids Research*, vol. 19, No. 21, (1991), pp. 5901–5905.

Daubendiek, Sarah L. et al., "Generation of Catalytic RNAs by Rolling Transcription of Synthetic DNA Nanocircles", *Nature Biotechnology*, vol. 15, (1997), pp. 273–277.

Daubendiek, Sarah L. et al., "Rolling–Circle RNA Synthesis: Circular Oligonucleotides as Efficient Substrates for T7 RNA Polymerase", *J. Am. Chem. Soc.*, vol. 117, (1995), pp. 7818–7819.

Fire, Andrew et al., "Rolling Replication of Short DNA Circles", *Proc. Natl. Acad. Sci.*, USA, vol. 92 (1995), pp. 4641–4645.

Kool, Eric T., "Circular Oligonucleotides: New Concepts in Oligonucleotide Design", *Annu. Rev. Biophys. Biomol. Struct.*, vol. 25 (1996), pp. 1–28.

Kool, Eric T., "Topologically Modified Biopolymers: Properties of Synthetic Circular DNAs and RNAs", *Trends Polym. Sci.*, vol. 3, No. 12, (1995), pp. 396–402.

Li, Ying et al., "Thermodynamics of DNA Duplexes with Adjacent G•A Mismatches", *Biochemistry*, vol. 30 (1991) pp. 7566–7572.

Vo. Thuong et al., "Targeting Pyrimidine Single Strands by Triplex Formation: Structural Optimization of Binding", *Nucleic Acids Research*, vol. 23, No. 15 (1995), pp. 2937–2944.

*Primary Examiner*—David Guzo

[57] ABSTRACT

A method is disclosed of amplifying the signal of target nucleic acid sequence analyte using a rolling circle replication mechanism and a bidirectional primer. The repeating signal amplification sequence units contain tags which are directly or indirectly detectable. In addition, methods of capturing the tagged complementary nucleic acid sequence of the target nucleic acid sequence onto an array surface and detecting the captured target nucleic acid sequences are disclosed. Kits are also disclosed for enhancing detection of target nucleic acid sequences using a mechanism of rolling circle replication and a bidirectional primer to attach to the complementary nucleic acid sequence of the target nucleic acid sequence a large number of detectable tags.

45 Claims, 3 Drawing Sheets

Repeating Signal Amplification Sequence

Figure 3

1% Denaturing Agarose Gel

SEQUENCE LISTING

```
<160> NUMBER OF SEQ ID NOS: 1

<210> SEQ ID NO 1
<211> LENGTH: 64
<212> TYPE: DNA
<213> ORGANISM: Artificial Sequence
<220> FEATURE:
<223> OTHER INFORMATION: Description of Artificial Sequence: A repeating
      series of four related  hairpin-loop structures.
      The c(gtaa)g loop sequence conforms to the known
      thermodynamically stable c(gnra)g class of loops.
<220> FEATURE:
<221> NAME/KEY: stem_loop
<222> LOCATION: (1)..(64)
<223> OTHER INFORMATION: There are four (4) stem_loop regions:  1-6 with
```

-continued

```
        16-11; 17-22 with 32-27; 33-38 with 48-43 and
        49-54 with 64-59
<220> FEATURE:
<221> NAME/KEY: repeat_unit
<222> LOCATION: (6)..(59)
<223> OTHER INFORMATION: There are four (4) repeating loop ends:  6-11;
        22-27; 38-43; and 54-59, having the sequence
        C(GTAA)G.
<220> FEATURE:
<221> NAME/KEY: misc_feature
<222> LOCATION: (8)..(56)
<223> OTHER INFORMATION: Tagged Thymidine residues at locations 8, 24,
        40, and 56 in loop end  structures.  Tag or label is fluorophore
        or radiolabel or a labeled bio-conjugate with biotinylated
        thymidine nucleotide.
<220> FEATURE:
<221> NAME/KEY: misc_feature
<222> LOCATION: (3)..(61)
<223> OTHER INFORMATION: Non-standard A-G and G-A base pairs are
        included in each hairpin loop at 3, 14; 4, 13; 19, 30; 20,
        29; 35, 46; 36, 45; 51, 62; and 52, 61.
<300> PUBLICATION INFORMATION:
<301> AUTHORS: Antao, V. P.
<302> TITLE: Unknown
<303> JOURNAL: Nucleic Acids Res.
<304> VOLUME: 21
<306> PAGES: 5901-5905
<307> DATE: 1991
<313> RELEVANT RESIDUES: 6 TO 11
<300> PUBLICATION INFORMATION:
<301> AUTHORS: Li, Y.
<302> TITLE: Unknown
<303> JOURNAL: Biochem. J.
<304> VOLUME: 30
<306> PAGES: 7566-7572
<307> DATE: 1991
<313> RELEVANT RESIDUES: 1 TO 16
<300> PUBLICATION INFORMATION:
<301> AUTHORS: Stolowitz, Mark L.
<302> TITLE: Phenylboronic Acid Complexing Reagents Derived From
<310> PATENT DOCUMENT NUMBER: 5,594,151
<311> PATENT FILING DATE: 1994-01-28
<312> PUBLICATION DATE: 1997-01-14
<313> RELEVANT RESIDUES: 8 TO 56
<300> PUBLICATION INFORMATION:
<301> AUTHORS: Kessler, C.
<302> TITLE: Advances in Mutagenesis Research
<303> JOURNAL: Book - Springer-Verlag, Berlin/Heidelberg
<306> PAGES: 105-152
<307> DATE: 1990
<313> RELEVANT RESIDUES: 8 TO 56

<400> SEQUENCE: 1
gcgagcgtaa gcgagcccga gcgtaagcga ggccgagcgt aagcgagggc gagcgtaagc    60
gagc                                                                64
```

METHOD OF AMPLIFYING THE SIGNAL OF TARGET NUCLEIC ACID SEQUENCE ANALYTE

FIELD OF THE INVENTION

This invention relates to a method of amplifying the signal of a target nucleic acid sequence analyte, and more particularly to a method of amplifying the signal of a target nucleic acid sequence analyte using a rolling circle replication mechanism and a bidirectional primer.

BACKGROUND OF THE INVENTION

Hybridization of target nucleic acid analyte to arrays of surface-bound nucleic acid sequence probes is an effective way to physically separate and detect defined nucleic acid sequences within a sample containing high sequence complexity. Array technology is particularly useful for monitoring cellular mRNA levels (gene expression), detecting and screening single mutation polymoiphisms, re-sequencing and potentially (de novo sequencing. The lower limit of detection of these array systems depends upon:

(1) the absolute number of target molecules in the analyte (either DNA or RNA);
(2) the number of target molecules in the analyte which are able to hybridize with the surface-bound nucleic acid sequence probes;
(3) the non-specific background binding; and
(4) the density (or total number) of the detectable tags in the target molecule.

There are a number of conventional methods to increase the absolute number of target molecules in the analyte. If the starting analyte is RNA, reverse transcription (RVT) followed by the polymerase chain reaction (PCR) or ligase chain reaction (LCR) may be used. If RNA is the desired final target, a combination of RVT/PCR followed by transcription with a phage RNA polymerase, such as T7 RNA polymerase, may be used. However, the exponential amplification obtained with RVT/PCR, for example, can significantly alter the final target distribution due to preferential amplification of certain mRNAs. Although this problem can be avoided by eliminating the PCR step and directly transcribing the reverse transcription cDNA product, transcription with T7 RNA polymerase routinely results in only about 100-fold target amplification. Unfortunately, this is unlikely to be sufficient to achieve the quantification and sensitivity required for gene expression systems for mRNA samples isolated from less than one million cells.

There are also a number of methods to increase the number of target molecules in an analyte that can effectively hybridize with the surface-bound nucleic acid probes. Reducing both the intramolecular structures of the target molecules and the probe molecules can facilitate the intermolecular hybridization process. When the application permits, this may be accomplished either by specifically designing the probes to have single-stranded character or by fragmenting the target molecules into shorter sequences, typically on the order of 50 to 100 nucleotides in length. Specific solutes, such as monovalent and divalent cations, polyamines and certain non-ionic detergents, may also facilitate hybridization by increasing the number of target molecules in the analyte that can effectively hybridize with the surface-bound nucleic acid probes.

Methods to decrease the non-specific background binding of the target directly depend upon the nature of the non-specific binding. Methods to decrease mis-hybridization of non-complementary targets to surface-bound probes generally involve decreasing mono- and divalent ion concentrations, addition of denaturants and increasing hybridization temperature. In addition to the latter two, addition of surfactants and carrier nucleic acid to the hybridization mixture may reduce non-specific binding of targets to the an-ay surface. Unfortunately, the tag moieties themselves can contribute to non-specific binding to both the allay surface and nucleic acid probes in ways that are not a priori apparent. Thus, having methodologies aimed at controlling and/or normalizing the chemical and structural environment of the tag molecules would be advantageous.

Methods to increase the density of the tag in the target molecules while suppressing dye-dye and base-dye quenching include:

(1) optimizing conventional techniques for direct incorporation of the tag, such as fluorescently-labeled nucleotides, into the target molecule; and
(2) utilizing improved techniques that employ a secondary hybridization event in which a common signal amplification probe having a tag or dye directly attached is hybridized to the mRNA or cDNA at a high multiplicity, such as the method disclosed in U.S. Pat. No. 5,124,246 to Chiron Corporation.

While these optimizations and improvements can result in substantially higher target tag densities than can be currently achieved by direct incorporation of tags into the targets, the added complexity of the secondary hybridization step is likely to prohibit the use of highly denaturing conditions during the target hybridization step. This may limit or even prohibit the use of secondary hybridization schemes with array formats that require higher stringency conditions such as cDNA-based arrays.

Finally, little attention has focused on controlling the spacing of the tag molecules within the targets. Clearly, little control over this factor is possible when employing conventional random tag-incorporation methods. Having a method that facilitates the spacing of the tags in a defined three-dimensional configuration, or at least at a defined distance from one another, has a number of advantages. For example, in the case where the tags are fluorescently-labeled dye molecules, defined spacing can significantly reduce any potential dye-dye or nucleotide-base quenching of the dye molecules. Reducing dye quenching and hence increasing their quantum efficiency effectively increases the amount of signal that can be detected from a given target molecule.

The methods and kits of the present invention solve many of the problems attendant with conventional techniques of improving the lower limit of detection of array systems. The methods and kits of the present invention involve the direct covalent attachment of a repeating signal amplification sequence containing a spatially-defined tag onto the target molecule using rolling circle replication employing a bidirectional primer.

The mechanism of rolling circle replication is known in the art. For example, PCT/US96/18812 discloses rolling circle replication for amplifying the amount of a target oligonucleotide. The replication reaction can be performed using tagged nucleotides to incorporate a detectable tag into the amplified target. PCT/US96/18812 also discloses using rolling circle replication in combination with an array for multiple testing of samples in parallel. In the examples of PCT/US96/18812, a ligase is used to circularize the amplification product, i.e., a linear amplification product is not hybridized. The application does not disclose using rolling circle replication for amplifying the signal produced by the target nucleic acid sequence.

The rolling circle mechanism is also described, for example, by A. Kornberg and T. A. Baker (editors), *DNA*

*Replication*, W. H. Freeman Publishing (1 992), page 113, wherein certain plant viroids and virusoids use a rolling circle mechanism to replicate their circular RNA genomes, and by A. Fire and S-Q Xu, *Proc. Nat. Acad. Scie. USA* 92, 4642–4645 (1995) and Liu et al., *J. Am. Chem. Soc.* 118, 1587–1594 (1996), wherein bacterial and phage DNA polymerases utilize small circular DNA (between 26 and 74 nucleotides long) as replication templates for synthesizing DNA products having a repeated sequence up to 12,000 nucleotides in length. In these references, the rolling circle mechanism is used in combination with DNA cleavage strategies to synthesize practical quantities of short, defined DNA oligonucleotides.

The use of bidirectional primers is also known in the art. For example, PCT/US96/05480 discloses a bidirectional primer for polymerase chain reaction amplification wherein the bidirectional primers are designed to be complementary to each end of the same target. In contrast, the methods and kits of the invention employ a bidirectional primer wherein a first end is complementary to a target nucleic acid sequence and a second end is complementary to a circular DNA template.

SUMMARY OF THE INVENTION

The invention is directed to a method of amplifying the signal of a target nucleic acid sequence analyte, including the steps of:

(1) hybridizing the first end of a bidirectional primer to a target nucleic acid sequence;

(2) polymerizing at the hybridized first end of the bidirectional primer to form the complementary nucleic acid sequence to the target nucleic acid sequence;

(3) hybridizing the second end of the bidirectional primer to a circular DNA template; and (4) polymerizing at the hybridized second end of the bidirectional primer using the circular DNA template in the presence of a multiplicity of signal amplification sequence units to form a complementary nucleic acid sequence to the target nucleic acid sequence to which is covalently attached a repeating signal amplification sequence, wherein the bidirectional primer contains a first end complementary to the target nucleic acid sequence and a second end complementary to the circular DNA template. Each repeating signal amplification sequence unit contains a tag which is directly or indirectly detectable. The invention is also directed to a kit for enhancing detection of a target nucleic acid sequence using a mechanism of rolling circle replication to attach to the target nucleic acid sequence a large number of detectable tags. In addition, the invention is directed to a method of capturing the tagged repeating target nucleic acid sequence onto an allay surface and detecting the captured target nucleic acid sequence.

DETAILED DESCRIPTION OF THE INVENTION

In this specification and in the claims which follow, reference will be made to a number of terms which shall be defined to have the following meaning:

The singular articles "a," "an," and "the" include plural referents unless the context clearly indicates otherwise.

The term "target nucleic acid sequence analyte" refers to a nucleic acid sequence whose presence or absence in a sample is desired to be detected.

The term "target nucleic acid sequence" refers to a unique nucleotide sequence in a target nucleic acid sequence analyte which is recognized by a capture probe.

The term "signal enhancement" or "signal amplification" refers to the signal intensity produced by the repeating signal amplification sequence relative to the signal intensity produced by a single signal amplification sequence unit attached to the target nucleic acid sequence analyte.

The term "tag" refers to a group of atoms or a molecule that is attached covalently to a nucleic acid sequence or other biological molecule for the purpose of detection by an appropriate detection system. The term "tagged cDNA" refers to cDNA to which a tag has been covalently attached. The term "tag" and "label" may be used interchangeably.

The term "oligonucleotide" refers to a short sequence of nucleotide monomers (usually 6 to 100 nucleotides)joined by phosphorus linkages (e.g., phosphodiester, alkyl and aryl-phosphate, phosphorothioate, phosphotliester), or non-phosphorus linkages (e.g., peptide, sulfamate and others). An oligonucleotide may contain modified nucleotides having modified bases (e.g., 5-methyl cytosine) and modified sugar groups (e.g., 2'-O-methyl ribosyl, 2'-O-methoxyethyl ribosyl, 2'-fluoro ribosyl, 2'-amino uibosyl, and the like). Oligonucleotides may be naturally-occurring or synthetic molecules of double- and single-stranded DNA and double- and single-stranded RNA with circular, branched or linear shapes and optionally including domains capable of forming stable secondary structures (e.g., stem-and-loop and loop-stem-loop structures).

The term "complement," "complementary" or "complementary nucleic acid sequence" refers to the nucleic acid strand that is related to the base sequence in another nucleic acid strand by the base-pairing rules.

The term "cDNA" refers to copy or complementary DNA and is a molecule that is complementary to a molecule of RNA. The cDNA may be either single-stranded or double-stranded.

The term "probe" refers to a single-stranded oligonucleotide sequence that will recognize and form a hydrogen-bonded duplex with a complementary sequence in a target nucleic acid sequence analyte or its cDNA derivative.

The term "hybrid" refers to a double-stranded nucleic acid molecule formed by hydrogen bonding between complementary nucleotides. The term "hybridize" refers to the process by which single strands of nucleic acid sequences form double-helical segments through hydrogen bonding between complementary nucleotides.

The term "capture probe" refers to a probe that possesses a sequence complementary to a predetermined region on the target nucleic acid sequence analyte and is capable of forming a stable hybrid with the target nucleic acid sequence analyte under selected stringency conditions. The capture probe is immobilized on a solid support for detection of the target nucleic acid sequence.

The term "aptamer" refers to any nucleic acid or non-nucleic acid chemical or biological compound that binds a defined target molecule through covalent, hydrogen-bonding, ionic and/or hydrophobic interactions.

The term "bio-conjugate" refers to a class of bio-molecules including, but not limited to, peptides, proteins, and antibodies that have been chemically detivatized with a tag.

The term "stringency" refers to hybridization conditions that affect the stability of hybrids, e.g., temperature, salt concentration, pH, formamide concentration and the like. These conditions are empirically optimized to maximize specific binding and minimize nonspecific binding of the capture probe to the target nucleic acid sequence analyte.

The term "poly A" refers to polyadenylic acid.

The term "poly T" refers to polythymidylic acid.

The term "hairpin" refers to an oligonucleotide structure having a single stranded loop attached to a double stranded stem.

The term "loop-stem-loop" refers to a "hairpin" enclosed by a loop. This structure can be formed from a circular oligonucleotide having two complementary binding domains joined by linkers that are not complementary with each other or to the other complementary binding domains. [See, e.g., Vo et al., Nucleic Acids Res. 23,2937–2944 (1995)].

The term "dNTP" refers to deoxynucleoside triphosphate and include the four naturally-occurring deoxynucleoside tiphosphates (DATP, dGTP, dCTP and dTTP).

The method of the invention employs the direct covalent attachment of repeating signal amplification sequence units onto a target nucleic acid sequence, usually an oligonucleotide, to amplify the signal produced by the target nucleic acid sequence analyte. The repeating signal amplification sequence contains a relatively large number of tags. The repeating signal amplification sequence units are attached to the target nucleic acid sequence via a mechanism of rolling circle replication using a bidirectional primer. Such mechanisms and primers are known in the art but heretofore have not been utilized in the manner contemplated by the method and products of the invention.

Figure 1:
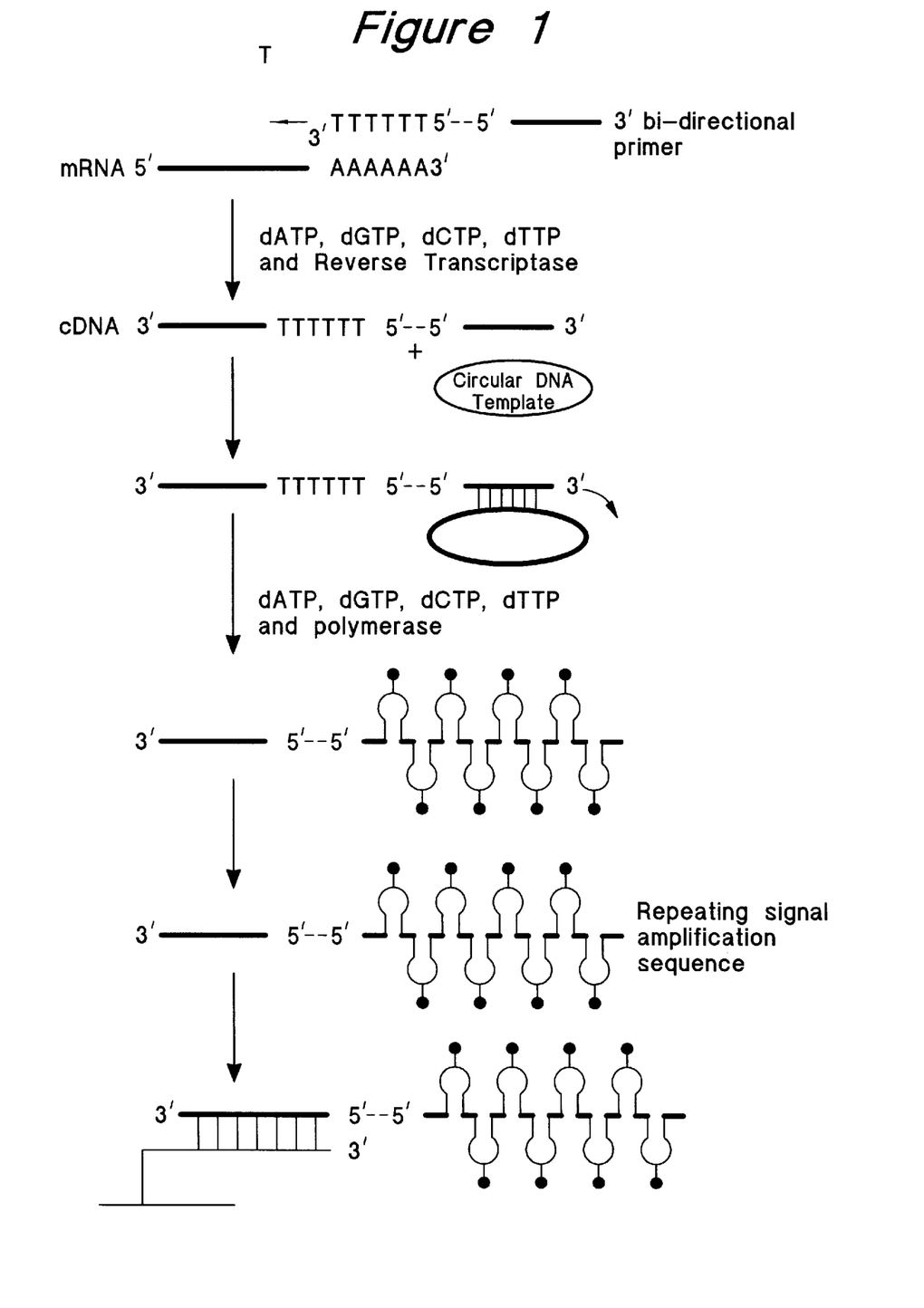
FIG. 1 is a schematic view of the four steps of the method of the invention for a preferred embodiment.

There are four basic steps for the method of the invention, which is described hereinafter with reference to FIG. 1 for a preferred embodiment:

Step 1

A target nucleic acid sequence is first hybridized to the first end of a bidirectional primer.

Step 2 cDNA of the target nucleic acid sequence analyte of interest is then polymerized using the hybridized bidirectional primer. In the preferred embodiment, cDNA of the mRNA extracted from the sample is synthesized by reverse transcriptase using a bidirectional primer.

Step 3

A circular DNA template is next hybridized to the second end of a bidirectional primer which has attached to its other end the cDNA of the target nucleic acid sequence.

Step 4

Finally, a multiplicity of signal amplification sequence units each containing at least one tag are polymerizing at the hybridized second end of the bidirectional primer using the circular DNA template to form the final product which is a cDNA to which is covalently attached a repeating signal amplification sequence. In the preferred embodiment, a repeating signal amplification sequence is covalently polymerized onto the 3' terminus of the cDNA by a DNA polymerase in the presence of dATP, dGTP, dCTP and a fluorescently tagged dTTP.

Step 5 (Optional)

The tagged cDNA is hybridized to the surface of a solid substrate, such as an array or a microscopic bead. The hybridization conditions must not disrupt the structure of the repeating signal amplification sequence which contributes to its detectability. In the preferred embodiment, the hybridization conditions must not disrupt the hair-pin-loop structure of the repeating signal amplification sequence.

Step 6 (Optional)

The signal from the repeating signal amplification sequence may be detected by any suitable means of detection. In the preferred embodiment, the tags incorporated into the repeating signal amplification sequence are fluorescent dye moieties that may be detected by monitoring the fluorescence emission at a defined set or range of wavelengths. The method of the invention is not strictly limited to the order of steps set forth above. Rather, it is contemplated that steps (1) and (2) may follow steps (3) and (4), such that the circular DNA template is first hybridized to the bidirectional primer. It is also conceivable that some applications may dictate that the signal amplification sequence be polymerized onto the target sequence subsequent to hybridization onto the surface-bound probe giving an overall step order of: (1), (2), (5), (3), (4), (6).

The methods and kits of the invention are described in terms of amplifying the signal of a target nucleic acid analyte. However, it is also contemplated that the methods and kits would be equally effective for amplifying the signal of other types of analytes that specifically bind an aptamer which, in turn, can be physically attached to or incorporated in place of the first end of the bidirectional primer. Suitable alternative analytes include amino acids, peptides, proteins, lipids, carbohydrates and other biological metabolites. The composition and form of the binding aptamer may be any chemical compound, such as, for example, nucleic acid, amino acid, peptides, proteins, carbohydrates, that may be synthesized either de novo, in combinatorial form, or selected from a random pool of similar compounds using defined selection protocols.

Bidirectional Primer

One of the keys to the invention is the use of a bidirectional primer having two functional ends wherein the first end is complementary to the target nucleic acid sequence and the second end is complementary to the circular DNA template. The primer has two functional 3'-termini formed by covalently joining together two standard oligonucleotides via a 5'—'5 phosphodiester linkage. The full-length primer can be obtained in a single synthesis using standard synthesis protocols and commercially available 5'-cyanoethyl- and 3'-cyanoethyl-phosphoramidites. Alternatively, each half of the primer can be synthesized individually using standard 3' to 5' synthesis protocols. The two primer halves could then be coupled together through their 5' termini using a number of conventional chemistries known in the air.

In the preferred embodiment, the first 3' terminus of the bidirectional primer contains a polyT sequence for hybridization to the 3' polyA tail of mRNA for the polymerization of cDNA wherein the second 3'-terminus contains a defined sequence for hybridization to the circular DNA template for polymerization of the signal amplification sequence. It is contemplated that the following alternate bidirectional primers may also be utilized, wherein:

(1) the first 3'-terminus may contain a defined sequence that targets a subclass of nucleic acids within a complex mixture, such as, for example, a related set of genes or mRNAs;

(2) the first 3'-terminus may contain a random polymer mixture representing all possible sequences of a given length for the purpose of hybridizing and priming polymerization at random positions along any target sequence; and (3) an aptamer is attached to the second half of the primer for the purpose of generating signal amplification of a target that binds the aptamer.

Synthesis of these classes of bidirectional primers would be facilitated by the "two-half" approach described above.

Circular DNA Template

Another key to the invention is the use of a circular DNA template to covalently attach the signal amplification sequence to the complementary nucleic acid sequence of the target nucleic acid sequence. The circular DNA templates useful in the method and kits of the invention are DNA molecules that:

(1) have a closed ring-type structure;

(2) are composed of nucleotides that can serve as templates for DNA polymerases and/or reverse transcriptase; and (3) are generally less than 100 nucleotides in total circumference. Examples of suitable circular DNA templates include those described in A. Fire and S-Q Xu, *Proc. Nat. Acad. Scie. USA* 92, 4642–4645 (1995) and Liu et al., *J. Am. Chem. Soc.* 118, 1587–1594 (1996).

Signal Amplification Sequence

The signal amplification sequence units useful in the methods and kits of the invention contain at least one tag. The final tagged analyte contains more than one repeating unit, preferably greater than about 10 repeating units, more preferably greater than about 100 tags, and most preferably greater than about 1,000 repeating units, which are directly or indirectly detectable.

Directly Detectable

Examples of directly detectable tags include nucleotides which are tagged or labeled fluorescently; radiolabeled, and detectable via light scattering techniques.

Indirectly Detectable

Examples of indirectly detectable tags include those detectable via binding or reacting with a bio-conjugate such as fluorescent, bioluminescent, chemiluminescent and light-scattering bio-conjugates. Suitable bio-conjugates include biotinylated nucleotides, such as biotinylated dNTP analogs and derivatives, to generate targets having multiple high affinity binding sites for the protein streptavidin. To achieve signal amplification, a fluorescently-labeled streptavidin or some other type of streptavidin-bioluminescent or chemiluminescent bio-conjugate may be bound to the biotinylated moiety within the signal amplification sequence. A suitable alternative method is the digoxigenin/anti-digoxigenin system involving the incorporation of a digoxigenin hapten nucleotide-derivative into the signal amplification sequence followed by specific binding of an fluorescently-labeled anti-digoxigenin anti-body conjugate [See C. Kessler, *Advances in Mutagenesis Research* (Obe, G. editor), Berlin/ Heidelberg: Springer-Verlag, pages 105–152(1990)]. The use of phenylboronic acid complexes forprepaling bio-conjugates as disclosed in U.S. Pat. No. 5,594,151 may also be used in the signal amplification method of the invention. It is also contemplated that thio-containing nucleotide tags may be incorporated at defined positions within the signal amplification sequence and subsequently detected by treatment with a thio-reactive fluorescently labeled dye derivative.

Definable Spacing of Tags

It is preferred that the tag be definably spaced, i.e., at defined positions either along the primary sequence of the nucleotide or three-dimensionally, within each signal amplification unit to reduce quenching, particularly when a fluorescent tag is used. Quenching refers to any process by which the fluorescence intensity of a given species is reduced. Fluorescence quenching due to complex formation (static quenching) occurs when the quenching species is bound to the fluorescent one, for example, by hydrophobic, charge-transfer and/or Van der Waals forces. In addition, quenching can be produced by the transfer of excited state energy from donor to acceptor molecule without the appearance of a photon (energy transfer). The effective energy transfer distance is a function of the lifetime of the excited state, the angular orientation of the donor and acceptor molecules, the refractive index of the solvent and the spectral overlap between donor and acceptor. The rate of energy transfer varies with the inverse sixth power of the distance between donor and acceptor out to about 5 nm, and beyond that, with the inverse seventh power. The distance at which half the excited state energy is transferred (i.e., fluorescence is reduced by 50%) is typically 2 to 5 nm (i.e., 20 to 50 Å), which is in the same range as the diameter of many proteins and the diameter of a nucleic acid double helix.

Fluorescent labeling of biological molecules must be carried out in a way that avoids self-quenching and energy-transfer quenching. Fluorescent self-quenching is produced by the stacking of planar hydrophobic regions of fluorophores at high local concentrations. These stacking interactions perturb the molecular orbital structures of the affected molecules and reduce their capacity for fluorescence emission. Thus, with increased fluorophore concentration, the incremental enhancement of fluorescence will decrease.

There are several strategies for dealing with the problem of complex formation which, to some extent will reduce other quenching effects as well. These include:

(1) making chemical modifications to the fluorescent species that do not affect their fluorescent properties but make it difficult for molecules to aggregate, and (2) attaching the fluorescent species to a polymeric structure which holds them apart.

The ability to keep fluorophores that are attached to a common polymer from contacting each other depends on the distance between the attachment points and the flexibility of the linkages. A double or triple helix structure such as a nucleic acid (or an agar polysacchaiide) provides a rigid framework with defined attachment points or regions. Nucleic acid duplexes and molecules of similar structure have persistence lengths of about 50 Å or more, wherein the persistence length is a measure of the statistical tendency of a polymer chain to remain in a straight line rather than coiled. To minimize other transfer mechanisms, the attached fluorophores should be spaced apart, preferably by 30 Å, more preferably by 50 Å, most preferably by 100 Å. For the closest fluorophores, the preferred angular orientation is near-orthogonal. For example, the bases in a DNA oligonucleotide can be tagged evenly fifth base. When bound to another complementary nucleic acid, the double-helix structure would then put adjacent labels on opposite sides of the helix, which is about 20 Å in diameter. With stiff linkers attaching the tag moieties to the polymer, the tags could easily be kept at least 30 Å apart. In many cases, this would suffice to reduce quenching to negligible levels. It should be clear that other spacing intervals, such as every third base, may be equally effective.

Figure 2:
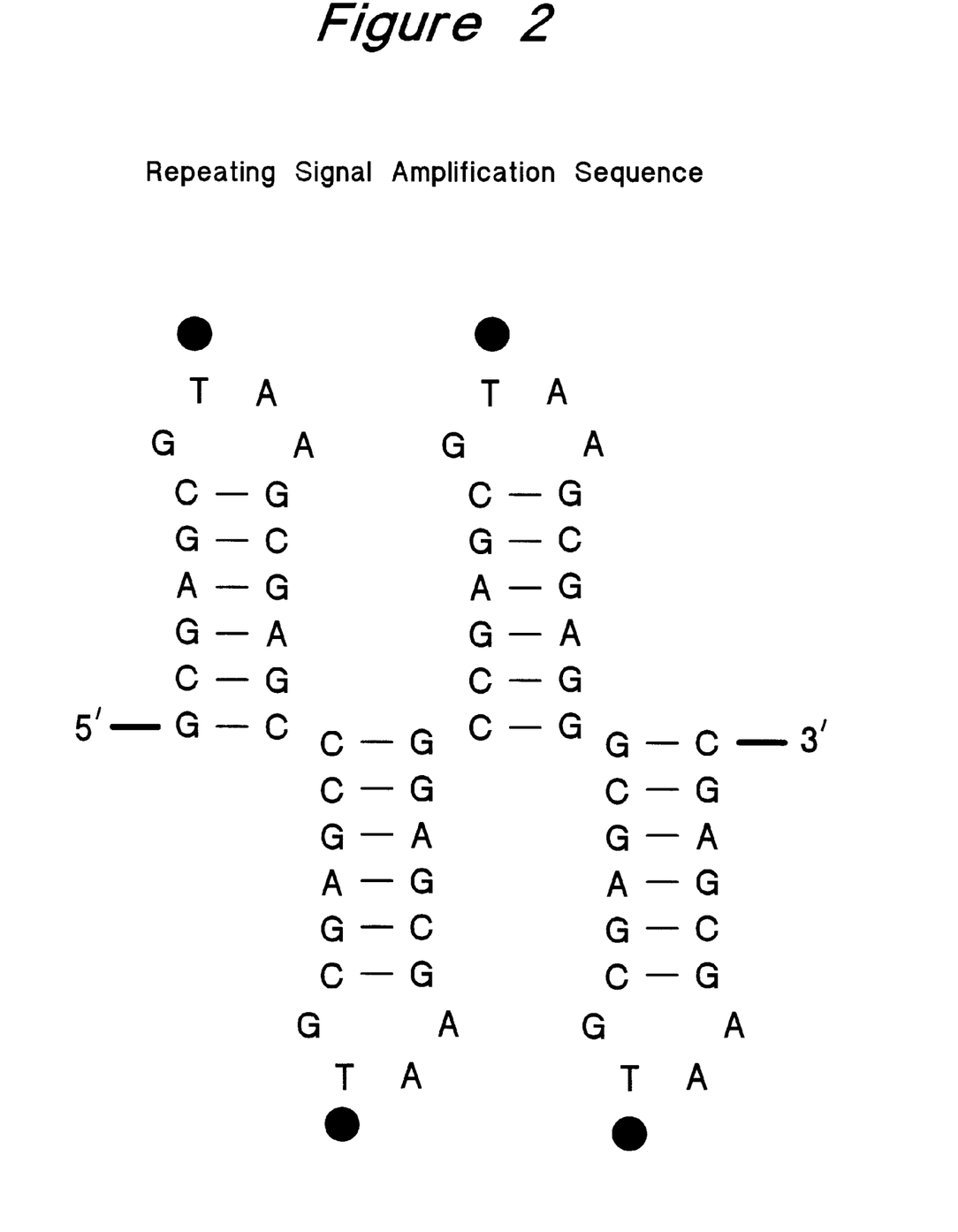
FIG. 2 shows a repeating signal amplification sequence containing a repeating unit of four related hairpin-loop structures (SEQ ID NO:1).

In FIG. 2, a preferred signal amplification sequence is composed of a repeating series of four related hairpin-loop structures. The C(GTAA)G loop sequence conforms to the known thermodynamically stable C(GNRA)G class of loops, as disclosed by V. P. Antao, *Nucleic Acids Res.* 21, 5901–5905 (1991), and the stem structures are composed of standard G-C base-pairs and two non-standard A-G and G-A base pairs that are known to be thermodynamically stable when presented in the given sequence context, as disclosed by Y. Li et al, *Biochemn.* 30, 7566–7572 (1991). In addition to forming stable hairpin-loop structures and thus reducing potential dye-dye quenching, this sequence possesses three additonal benefits:

(1) The fluorescently-tagged thymidine residue resides at the a loop position that is predicted to not be involved in any base stacking or hydrogen bonding interactions. This spatial geometry forces the dye moiety away from hairpin-loop structure thereby reducing potential base-dye energy transfer and hence fluorescence quenching.

(2) Because thymine-type residues exist only at a single position within the loop of the hairpin-loop structures, it is not necessary to dope the polymerization reaction with dTTP. This allows greater latitude of reaction conditions to be employed for optimum incorporation of the fluorescently tagged-dTTP.

(3) The inclusion of non-standard A-G and G-A base pairs within the given sequence context of the stem structures results in the complementary circular DNA template not having any predicted stable secondary structure. Having an unstructured circular DNA template is likely to facilitate both the hybridization and subsequent polymerization reactions.

The amount of signal amplification that may be achieved by the method and products of the invention is dependent upon the efficiency with which the polymerase incorporates the signal amplification sequence units containing a tag. In general, fluorescently-tagged signal amplification sequence units are less efficiently incorporated than the naturally-occurring sequences equivalent to signal amplification sequence units. In addition, the fluorescently-tagged signal amplification sequence units have a propensity to act as chain terminators or pseudo-chain terminators by inhibiting further polymerization once a single tagged signal amplification sequence unit has been incorporated into the growing polynucleotide sequence.

However, the methods and kits of the invention are useful tools even if conditions for the efficient incorporation of specific nucleotide derivatives cannot be identified. For example, the method of the invention may be used to generate a defined repeated DNA sequence containing only the four naturally-occurring bases where signal amplification may be achieved by hybridizing a fluorescently tagged probe to this defined sequence. Further, the method of the invention may be used to generate cDNA targets having a repeating sequence and/or structure corresponding to high affinity binding sites for known nucleic acid binding proteins using only the four naturally-occurring dNTPs where signal amplification may be achieved by binding a chemiluminescent or bioluminescent derivative of the corresponding specific nucleic acid binding protein.

While the method and kits of the invention have been described in terms of surface-bound nucleic acid arrays, it is contemplated that the methods and kits of the invention would also be applicable for use with solution-based systems.

It should be understood that the above description is intended to illustrate and not limit the scope of the invention. Other aspects, advantages and modifications within the scope of the invention will be apparent to those skilled in the art to which the invention pertains.

The following examples are put forth so as to provide those of ordinary skill in the art with a complete disclosure and description of how to make and use the method and products of the invention, and are not intended to limit the scope of what the inventors regard as their invention.

EXAMPLES

Example 1

Figure 3:
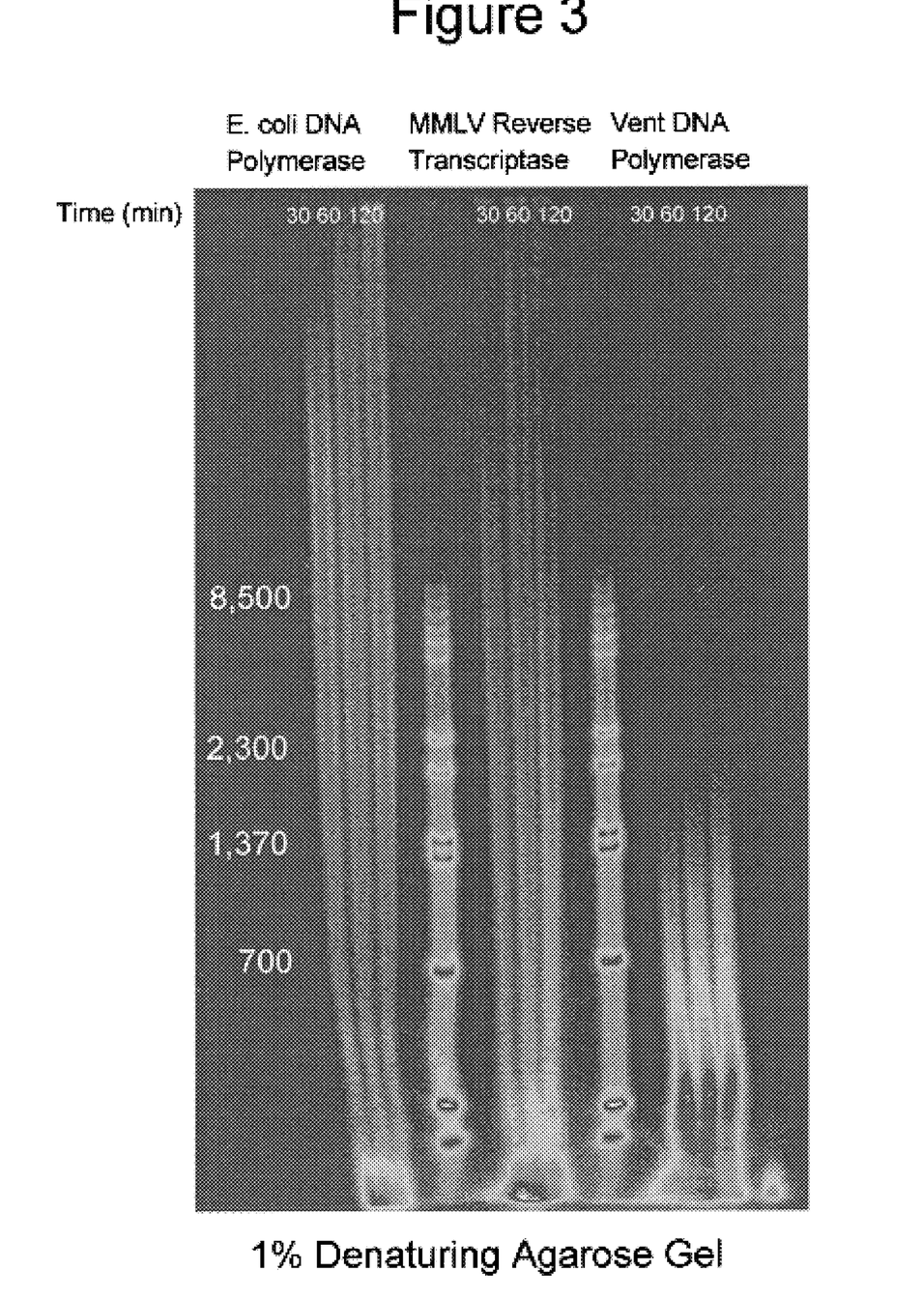
FIG. 3 shows the results for three different polymerases which were tested for their ability to extend a $^{32}$P-labeled primer that was hybridized to a 64 nucleotide circular DNA template in the presence of all four natural dNTPs.

Three different polymerases [Klenow fragment of E. coli DNA polymerase (3'exo-), MMLV reverse transcriptase, Vent (3'exo-) DNA polymerase] were tested for their ability to extend a $^{32}$P-labeled primer that was hybridized to a 64 nucleotide circular DNA template in the presence of all four natural dNTPs. The results are shown in FIG. 3.

Native agarose gel electrophoresis indicated that under the reaction conditions tested, the Klenow fragment of E. Coli DNA polymerase (3'exo-) catalyzed the polymerization of longer DNA products that did either the MMLV reverse transcriptase or Vent (3'exo-) DNA polymerase. Although the length of DNA product pool was heterogeneous, the average length was about 8,500 nucleotides which corresponds to about 500 hairpin-loop structures (16 repeating signal amplification units). This indicates a possible 500 fold signal amplification if reaction conditions and/or a polymerase mutant can be identified that facilitates the efficient incorporation of fluorescently labeled dNTP analogs into product.

While the invention has been described and illustrated with reference to specific embodiments, those skilled in the art will recognize that modification and variations may be made without departing from the principles of the invention as described herein above and set forth in the following claims.

What is claimed is:

1. A method of amplifying the signal of target nucleic acid sequence analyte, comprising the steps of:

(1) hybridizing a first end of a bidirectional primer to a target nucleic acid sequence;

(2) polymerizing at said hybridized first end of said bidirectional primer to form a complementary nucleic acid sequence of said target nucleic acid sequence;

(3) hybridizing a second end of said bidirectional primer to a circular DNA template; and (4) polymerizing at said hybridized second end of said bidirectional primer using said circular DNA template in the presence of a multiplicity of signal amplification sequence units to form a complementary nucleic acid sequence of said target nucleic acid sequence to which are covalently attached said repeating signal amplification sequence units, wherein said bidirectional primer contains a first end complementary to said target nucleic acid sequence and a second end complementary to said circular DNA template.

2. A method of amplifying the signal of target nucleic acid sequence analyte, comprising the steps of:

(1) hybridizing a first end of a bidirectional primer to a circular DNA template;

(2) polymerizing at said hybridized first end of said bidirectional primer using said circular DNA template in the presence of a multiplicity of signal amplification sequence units to form a complementary nucleic acid sequence of said target nucleic acid sequence to which are covalently attached said repeating signal amplification sequence units;

(3) hybridizing a second end of said bidirectional primer to a target nucleic acid sequence; and (4) polymerizing at said hybridized second end of said bidirectional primer to form a complementary nucleic acid sequence of said target nucleic acid sequence, wherein said bidirectional primer contains a first end complementary to said circular DNA template and a second end complementary to said target nucleic acid sequence.

3. The method of claim 1 wherein said bidirectional primer comprises a nucleic acid aptamer.

4. The method of claim 2 wherein said bidirectional primer comprises a nucleic acid aptamer.

5. The method of claim 1 wherein said bidirectional primer comprises a non-nucleic acid aptamer.

6. The method of claim 2 wherein said bidirectional primer comprises a non-nucleic acid aptamer.

7. The method of claim 1 wherein said repeating signal amplification sequence contains more than one repeating unit.

8. The method of claim 2 wherein said repeating signal amplification sequence contains more than one repeating unit.

9. The method of claim 1 wherein said repeating signal amplification sequence contains greater than about 10 repeating units.

10. The method of claim 2 wherein said repeating signal amplification sequence contains greater than about 10 repeating units.

11. The method of claim 1 wherein said repeating signal amplification sequence contains greater than about 100 repeating units.

12. The method of claim 2 wherein said repeating signal amplification sequence contains greater than about 100 repeating units.

13. The method of claim 1 wherein said repeating signal amplification sequence contains greater than about 1,000 repeating units.

14. The method of claim 2 wherein said repeating signal amplification sequence contains greater than about 1,000 repeating units.

15. The method of claim 1 wherein said complementary nucleic acid sequence is cDNA.

16. The method of claim 2 wherein said complementary nucleic acid sequence is cDNA.

17. The method of claim 1 wherein said signal amplification sequence units are directly detectable.

18. The method of claim 2 wherein said signal amplification sequence units are directly detectable.

19. The method of claim 17 wherein said signal amplification sequence units are tagged nucleotides selected from the group consisting of fluorescently-tagged nucleotides, radiolabeled nucleotides and nucleotides detectable via light scattering.

20. The method of claim 18 wherein said signal amplification sequence units are tagged nucleotides selected from the group consisting of fluorescently-tagged nucleotides, radiolabeled nucleotides and nucleotides detectable via light scattering.

21. The method of claim 1 wherein said signal amplification sequence units are indirectly detectable.

22. The method of claim 2 wherein said signal amplification sequence units are indirectly detectable.

23. The method of claim 21 wherein said signal amplification sequence units are detectable via binding or reacting with a bio-conjugate selected from the group consisting of fluorescent, bioluminescent, chemiluminescent and light-scattering bio-conjugates.

24. The method of claim 22 wherein said signal amplification sequence units are detectable via binding or reacting with a bio-conjugate selected from the group consisting of fluorescent, bioluminescent, chemiluminescent and light-scattering bio-conjugates.

25. The method of claim 21 wherein said signal amplification sequence units comprise a biotinylated nucleotide.

26. The method of claim 22 wherein said signal amplification sequence units comprise a biotinylated nucleotide.

27. The method of claim 25 wherein said biotinylated nucleotide is a thio-containing nucleotide.

28. The method of claim 26 wherein said biotinylated nucleotide is a thio-containing nucleotide.

29. The method of claim 1 wherein said signal amplification sequence units comprise a tag which is definably spaced along a primary sequence of said signal amplification sequence to reduce quenching.

30. The method of claim 2 wherein said signal amplification sequence units comprise a tag which is definably spaced along a primary sequence of said signal amplification sequence to reduce quenching.

31. The method of claim 1 wherein said signal amplification sequence units comprise a tag which is definably spaced in three dimensions to reduce quenching.

32. The method of claim 2 wherein said signal amplification sequence units comprise a tag which is definably spaced in three dimensions to reduce quenching.

33. The method of claim 1 wherein said signal amplification sequence units comprise a sequence of naturally-occurring nucleotides complementary to a DNA-binding protein.

34. The method of claim 2 wherein said signal amplification sequence units comprise a sequence of naturally-occurring nucleotides complementary to a DNA-binding protein.

35. The method of claim 1 further comprising the step of hybridizing said complementary nucleic acid sequence of said target nucleic acid sequence to which are covalently attached said repeating signal amplification sequence units to a capture probe on an array surface.

36. The method of claim 2 further comprising the step of hybridizing said complementary nucleic acid sequence of said target nucleic acid sequence to which are covalently attached said repeating signal amplification sequence units to a capture probe on an array surface.

37. The method of claim 35 further comprising the step of detecting a signal from said repeating signal amplification sequences units.

38. The method of claim 36 further comprising the step of detecting a signal from said repeating signal amplification sequences units.

39. A kit for carrying out the signal amplification method of claim 1, comprising:
   a. a circular DNA template;
   b. a bidirectional primer having a first end complementary to said target nucleic acid sequence and a second end complementary to said circular DNA template; and
   c. a multiplicity of four naturally-occurring dNTPs wherein at least one of said dNTPs is tagged.

40. A kit for carrying out the signal amplification method of claim 2, comprising:
   a. a circular DNA template,
   b. a bidirectional primer having a first end complementary to said target nucleic acid sequence and a second end complementary to said circular DNA template; and
   c. a multiplicity of four naturally-occurring dNTPs wherein at least one of said dNTPs is tagged.

41. A kit for carrying out the signal amplification method of claim 35, comprising:

a. an array containing a multiplicity of capture probes;

b. a circular DNA template;

c. a bidirectional primer having a first end complementary to said target nucleic acid sequence and a second end complementary to said circular DNA template; and d. a multiplicity of four naturally-occurring dNTPs wherein at least one of said dNTPs is tagged.

42. A kit for carrying out the signal amplification method of claim 36, comprising:

a. an array containing a multiplicity of capture probes;

b. a circular DNA template;

c. a bidirectional primer having a first end complementary to said target nucleic acid sequence and a second end complementary to said circular DNA template, and d. a multiplicity of four naturally-occurring dNTPs wherein at least one of said dNTPs is tagged.

43. A kit for carrying out the signal amplification method of claim 37, comprising:

a. an array containing a multiplicity of capture probes;

b. a circular DNA template;

c. a bidirectional primer having a first end complementary to said target nucleic acid sequence and a second end complementary to said circular DNA template, and d. a multiplicity of four naturally-occurring dNTPs wherein at least one of said dNTPs is tagged.

44. A kit for carrying out the signal amplification method of claim 38, comprising:

a. an array containing a multiplicity of capture probes;

b. a circular DNA template;

c. a bidirectional primer having a first end complementary to said target nucleic acid sequence and a second end complementary to said circular DNA template; and d. a multiplicity of four naturally-occurring dNTPs wherein at least one of said dNTPs is tagged.

45. An array for detecting target nucleic acid sequences, comprising:

a. a substrate having a surface;

b. a multiplicity of capture probes attached to said surface of said substrate; and c. a multiplicity of complementary nucleic acid sequences of said target nucleic acid sequences to which are covalently attached repeating signal amplification sequence units.

* * * * *